United States Patent [19]
Griffith

[11] Patent Number: 5,766,249
[45] Date of Patent: *Jun. 16, 1998

[54] TISSUE BONDABLE CYSTOSTOMY TUBE AND METHOD OF CYSTOSTOMY TUBE IMPLANTATION

[76] Inventor: Donald P. Griffith, 5696 Longmont, Houston, Tex. 77056

[*] Notice: The portion of the term of this patent subsequent to Nov. 20, 2010, has been disclaimed.

[21] Appl. No.: 759,932

[22] Filed: Dec. 4, 1996

Related U.S. Application Data

[63] Continuation of Ser. No. 499,853, Jul. 10, 1995, abandoned, which is a continuation of Ser. No. 101,923, Aug. 4, 1993, abandoned, which is a continuation-in-part of Ser. No. 615,896, Nov. 20, 1990, Pat. No. 5,234,408.

[51] Int. Cl.$^6$ .............................. A61F 2/02; A61M 39/10
[52] U.S. Cl. ........................... 623/12; 600/30; 604/93; 604/175
[58] Field of Search ................... 623/11, 12; 604/175, 604/93, 174; 600/30

[56] References Cited

U.S. PATENT DOCUMENTS

| | | | |
|---|---|---|---|
| 3,540,451 | 11/1970 | Zeman . | |
| 3,717,151 | 2/1973 | Collett . | |
| 3,721,229 | 3/1973 | Panzer | 604/174 X |
| 4,004,298 | 1/1977 | Freed | 623/11 |
| 4,025,964 | 5/1977 | Owens | 623/11 |
| 4,217,664 | 8/1980 | Faso . | |
| 4,217,899 | 8/1980 | Freier | 600/30 X |
| 4,338,937 | 7/1982 | Lerman . | |
| 4,400,169 | 8/1983 | Stephen | 604/93 X |
| 4,438,773 | 3/1984 | Letterio | 606/151 |
| 4,534,761 | 8/1985 | Raible . | |
| 4,555,242 | 11/1985 | Saudager | 604/96 |
| 4,623,348 | 11/1986 | Feit . | |
| 4,642,104 | 2/1987 | Sakamoto et al. . | |
| 4,654,033 | 3/1987 | Lapeyre et al. | 604/175 |
| 4,781,176 | 11/1988 | Ravo . | |
| 4,781,694 | 11/1988 | Branemark et al. | 604/175 |
| 4,813,967 | 3/1989 | Renard et al. | 623/66 |
| 4,863,438 | 9/1989 | Gauderer et al. . | |
| 4,897,081 | 1/1990 | Poirier et al. | 604/175 |
| 4,931,056 | 6/1990 | Ghajar et al. | 606/130 |
| 4,934,999 | 6/1990 | Bader . | |
| 4,959,054 | 9/1990 | Heimke et al. . | |
| 4,976,735 | 12/1990 | Griffith et al. . | |
| 5,007,900 | 4/1991 | Picha et al. . | |
| 5,013,717 | 5/1991 | Solomon et al. . | |
| 5,019,393 | 5/1991 | Ito et al. . | |
| 5,035,711 | 7/1991 | Aoki et al. . | |
| 5,064,417 | 11/1991 | Andreussi | 604/175 |
| 5,234,408 | 8/1993 | Griffith | 604/93 |
| 5,257,973 | 11/1993 | Villasuso | 604/49 |
| 5,290,251 | 3/1994 | Griffith | 604/175 |
| 5,391,156 | 2/1995 | Hildwein et al. | 604/174 |

FOREIGN PATENT DOCUMENTS

| | | | |
|---|---|---|---|
| 0194980 | 9/1986 | European Pat. Off. . | |
| 0343114 | 11/1989 | European Pat. Off. | 604/174 |
| 2105197 | 3/1983 | United Kingdom | 623/26 |
| 8601729 | 3/1986 | WIPO . | |
| 8706122 | 10/1987 | WIPO | 623/11 |

OTHER PUBLICATIONS

Campbell's Urology, published by W.B. Saunders Co., 5th Edition, pp. 2116–2119.
Atlas of Urologic Surgery, published by W.B. Saunders Co., 1989, authored by Frank Hinman, Jr., pp. 505–507.
Urologic Surgery, 2nd Edition, published by Harber & Row, edited by James Glenn and William Boyce, pp. 304–305.
Catalog from Bard Urological Division, C.R. Bard, Inc., Covington, GA 30209.
Publication from Cook Urological, Inc., 1100 West Morgan Street, P.O. Box 227, Spencer, IN 47460.

*Primary Examiner*—David H. Willse
*Attorney, Agent, or Firm*—Rosenblatt & Redano P.C.

[57] ABSTRACT

The present invention relates to a tissue bondable cystostomy tube for use in a human patient. The present invention also relates to a method for surgically implanting the tissue bondable cystostomy tube in a human patient.

13 Claims, 5 Drawing Sheets

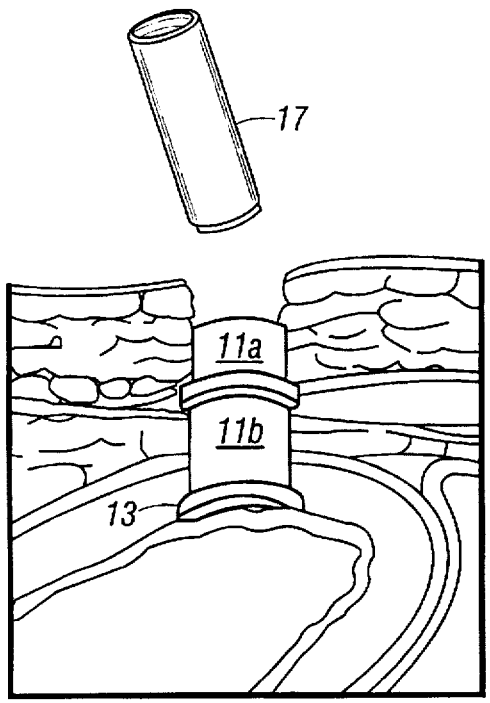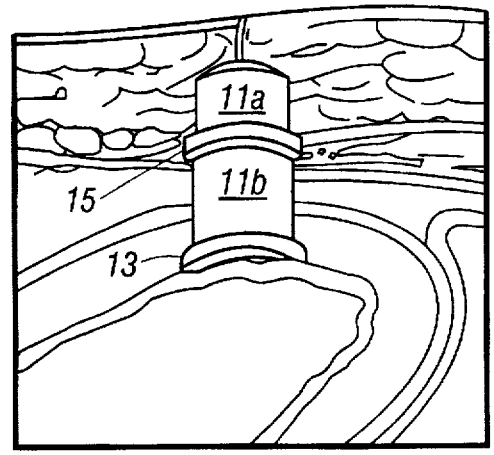
Figure 1A
Figure 1B
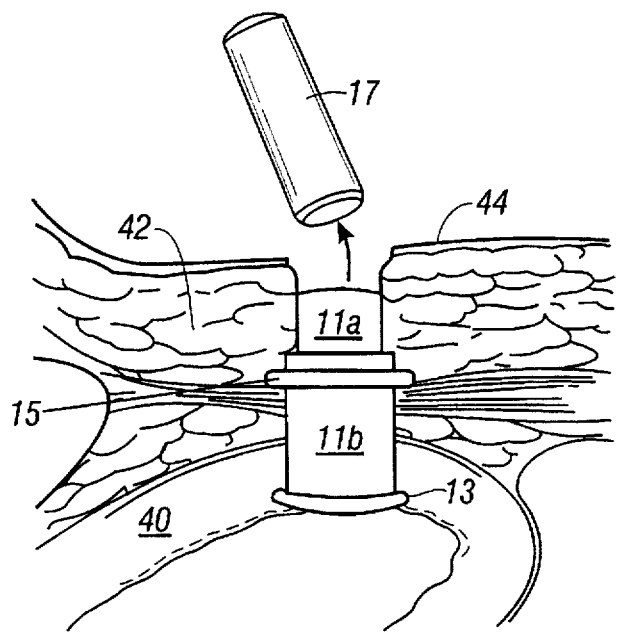
Figure 2

TISSUE BONDABLE CYSTOSTOMY TUBE AND METHOD OF CYSTOSTOMY TUBE IMPLANTATION

RELATED APPLICATIONS

This application is a continuation of U.S. application Ser. No. 08/499,853, filed on Jul. 10, 1995, now abandoned, which is a continuation of U.S. application Ser. No. 08/101,923, filed on Aug. 4, 1993, now abandoned, which is a continuation-in-part of U.S. application Ser. No. 07/615,896, filed on Nov. 20, 1990, now U.S. Pat. No. 5,234,408.

BACKGROUND OF THE INVENTION

1. Field of the Invention

The present invention relates to a tissue bondable cystostomy tube for use in a human patient. The invention, more particularly, concerns a tissue bondable cystostomy tube comprising (1) a flanged deep implant cylinder, (2) a transcutaneous hollow cylinder, and (3) a cap and drainage tube assembly.

The present invention also relates to the surgical procedure for implantation of the tissue bondable cystostomy tube. This procedure entails implantation of the device in a patient, bonding of the patient's tissue to portions of the device, and activation of the device.

2. Description of the Prior Art

Cystostomy tubes have been known for many years. Cystostomy refers to the formation of an opening into the bladder. Cystostomy tubes are inserted into the opening in the bladder resulting from the cystostomy in order to provide a flow path for fluid contained in the bladder to a point external to the patient's body.

One of the oldest forms of cystostomy is suprapubic cystostomy. Suprapubic cystostomy is described in *Cambell's Urology*, 5th ed., W. B. Saunders Co. (1986), at page 2117.

There are many problems associated with suprapubic cystostomy. In some cases the bladder contracts down on the cystostomy tube and causes a ureterovesical obstruction. Another problem with suprapubic cystostomy results from the leakage of urine around the cystostomy tube and onto abdominal skin. Similarly, skin bacteria gain access to the urinary bladder resulting in urinary infection.

Another form of cystostomy is percutaneous cystostomy. Percutaneous cystostomy is described in *Cambell's Urology*, 5th edition, W. B. Saunders Co. (1986), at page 2117. Percutaneous cystostomy is sometimes referred to as "punch cystostomy." Percutaneous cystostomy also results in urinary leakage around the cystostomy tube onto the abdominal skin, and skin bacteria gain access to the urinary bladder. Percutaneous cystostomy thus also results in urinary infection.

Another problem plaguing prior art cystostomy tubes is the inability of the tubes to bond with the tissue due to movement of the tubes within the body. The present invention solves this problem through the use of a planer-like disc or flange at its base. This stabilizing flange minimizes shifting of the cystostomy tube and enhances the probability that tissue bonding will take place. The present invention further enhances tissue bonding by coating portions of the cystostomy tube with a material suitable for bonding with biological tissue.

SUMMARY OF THE INVENTION

The present invention provides a tissue bondable cystostomy tube which overcomes the problems of the prior art cystostomy tubes. The cystostomy tube of the present invention comprises (1) a deep implant cylinder having an upper end, a lower end, and a planar disc-like base, (2) a transcutaneous hollow cylinder having a flanged upper end and a lower end, and (3) an occlusive cap and drainage tube assembly. The lower portion of the deep implant cylinder, including the planar disc-like base, is coated on its exterior surface with a material suitable for bonding with biological tissue, such as a polytetrafluoroethylene polymer. The upper portion of the deep implant cylinder is made of silicon and is uncoated.

The planar disc-like base of the deep implant cylinder extends radially outward from the lower end of the deep implant cylinder and provides a means for positioning and aligning the deep implant cylinder with the bladder membrane.

The lower end of the transcutaneous hollow cylinder is slidably received into the upper end of the deep implant cylinder. When implanted in the patient, the flanged upper end of the transcutaneous hollow cylinder is flush mounted with the surface of the patient's abdomen. A removable cap and drainage tube assembly can be inserted in the upper end of the transcutaneous hollow cylinder.

The present invention also encompasses a method for implanting the apparatus described herein. This is a multi-step method, first involving surgical implantation of the deep implant cylinder in the region of the bladder membrane. During this initial implantation phase, a plug is inserted in the deep implant cylinder. The deep implant cylinder remains in the patient for a sufficient period of time for tissue bonding to occur.

In the second phase of the implantation process, skin above the deep implant cylinder is removed and the plug is removed from the deep implant cylinder. The transcutaneous hollow cylinder is then inserted into the deep implant cylinder until the lower end of the transcutaneous hollow cylinder is adjacent the bladder wall. The combined deep implant cylinder and transcutaneous hollow cylinder remain in the patient for several weeks.

In the third phase of the implantation process, the transcutaneous hollow cylinder is replaced with another transcutaneous hollow cylinder of sufficient length to extend into the bladder. During this phase, the device is activated.

BRIEF DESCRIPTION OF THE DRAWINGS

FIG. 1a is a side view of the present invention during the implantation of the deep implant cylinder and plug.

FIG. 1b is a side view of an implanted deep implant cylinder and plug during the step in the surgical procedure when tissue bonding is occurring.

FIG. 2 is a side view of the deep implant cylinder during the second phase of the implantation process when the plug is removed.

DESCRIPTION OF THE PREFERRED EMBODIMENT

Figure 4:
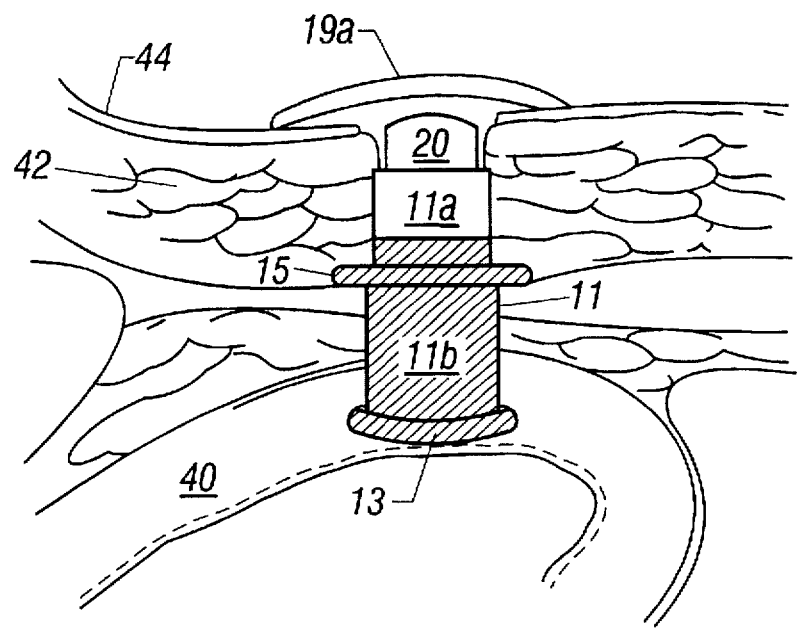
FIG. 4 is a side view of the deep implant cylinder and transcutaneous hollow cylinder as installed in the second phase of the surgical implantation process.

The deep implant cylinder 11, having an upper end or portion and a lower end or portion is shown in FIGS. 1a, and 1b. A planar disc-like base 13 extends radially outward from the lower end of the deep implant cylinder 11. As shown in FIG. 4, the planar disc-like base 13 has a substantially constant radial dimension. As shown in FIGS. 1a, and 1b, the deep implant cylinder 11 is divided into two regions, 11a and 11b. The lower portion of the deep implant, 11b, is coated on its exterior surface with a material suitable for bonding with biological tissue. As shown in FIGS. 1a and 1b the lower portion of the deep implant cylinder terminates at a lower end point. The upper portion of the deep implant, 11a, is made of a nonporous material, such as polyurethane, polytetrafluroethylene, or silicone and is uncoated. The planar disc-like base 13, is also coated on its exterior surface with a material suitable for bonding with biological tissue. In a preferred embodiment, the planar disc-like base 13 is integrally formed with the deep implant cylinder 11.

In a preferred embodiment, a stabilizing flange 15 is slidably mounted on the exterior surface of the deep implant cylinder 11. The stabilizing flange 15 is coated on its exterior surface with a material suitable for bonding with biological tissue. The desirability of using the stabilizing flange 15 varies on a case-by-case basis. The stabilizing flange 15 secures the deep implant cylinder to the abdominal wall.

During the initial stage of the method for implanting the tissue bondable cystostomy tube, a plug 17 is inserted in the deep implant cylinder 11, as shown in FIG. 1a. In a preferred embodiment, the plug 17 is made from a material such as Teflon®. Plug 17 comprises female threads in its upper end. These female threads provide for easy installation and removal of plug 17, using a male threaded tool having a diameter and thread size that will mate with the female threads of plug 17. The remainder of plug 17 below the female threaded section is solid.

Figure 3A:
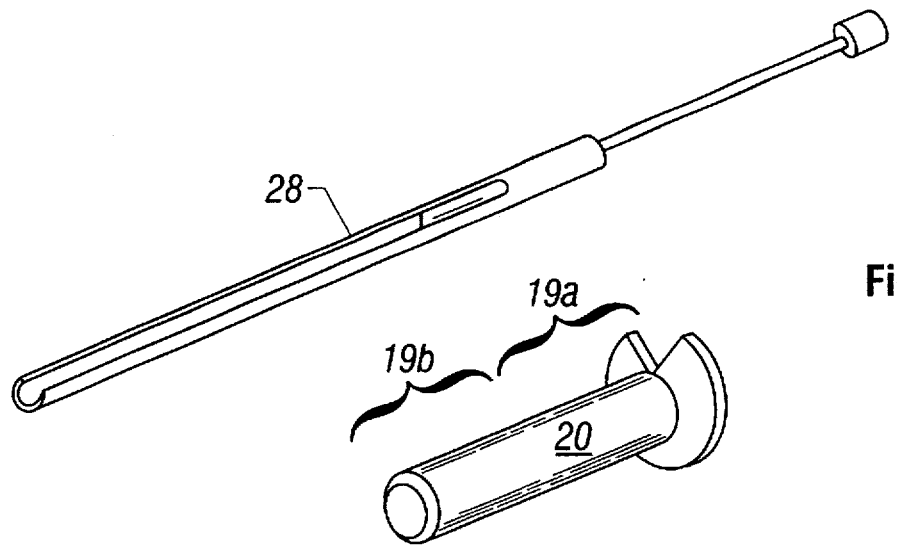
FIG. 3a is an isometric view of a transcutaneous hollow cylinder and crimping tool.
Figure 5:
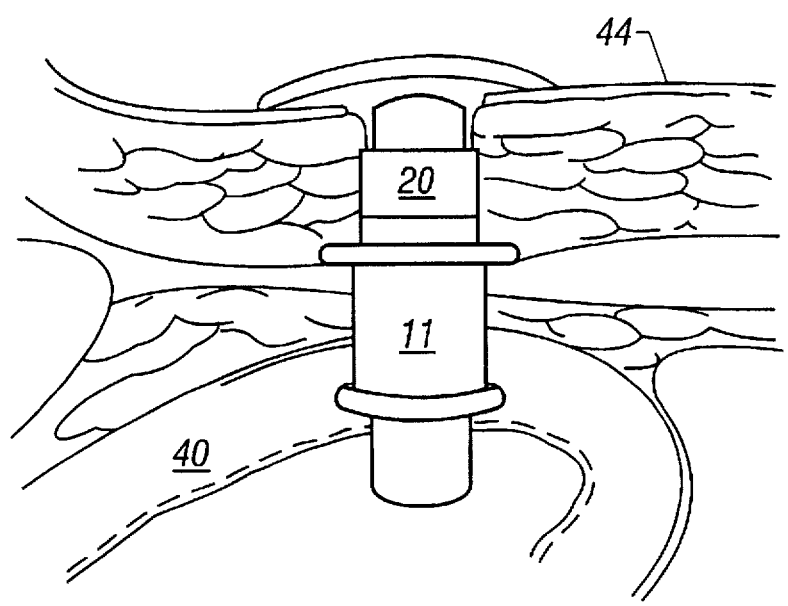
FIG. 5 is a side view of the deep implant cylinder and replacement transcutaneous hollow cylinder as installed in the last phase of the implantation process.

Referring to FIGS. 3a, 4, and 5, a transcutaneous hollow cylinder 20, having a flanged upper end 19a and a lower end 19b, is inserted in the upper end of the deep implant cylinder 11. As shown in FIG. 3a, the lower end of the transcutaneous hollow cylinder is open. In a preferred embodiment, the flanged upper end of the transcutaneous hollow cylinder comprises a V-shaped notch, as shown in FIG. 3a. This notch provides for easier crimping of the transcutaneous hollow cylinder thereby enabling it to be more easily inserted into the deep implant cylinder.

Figure 6:
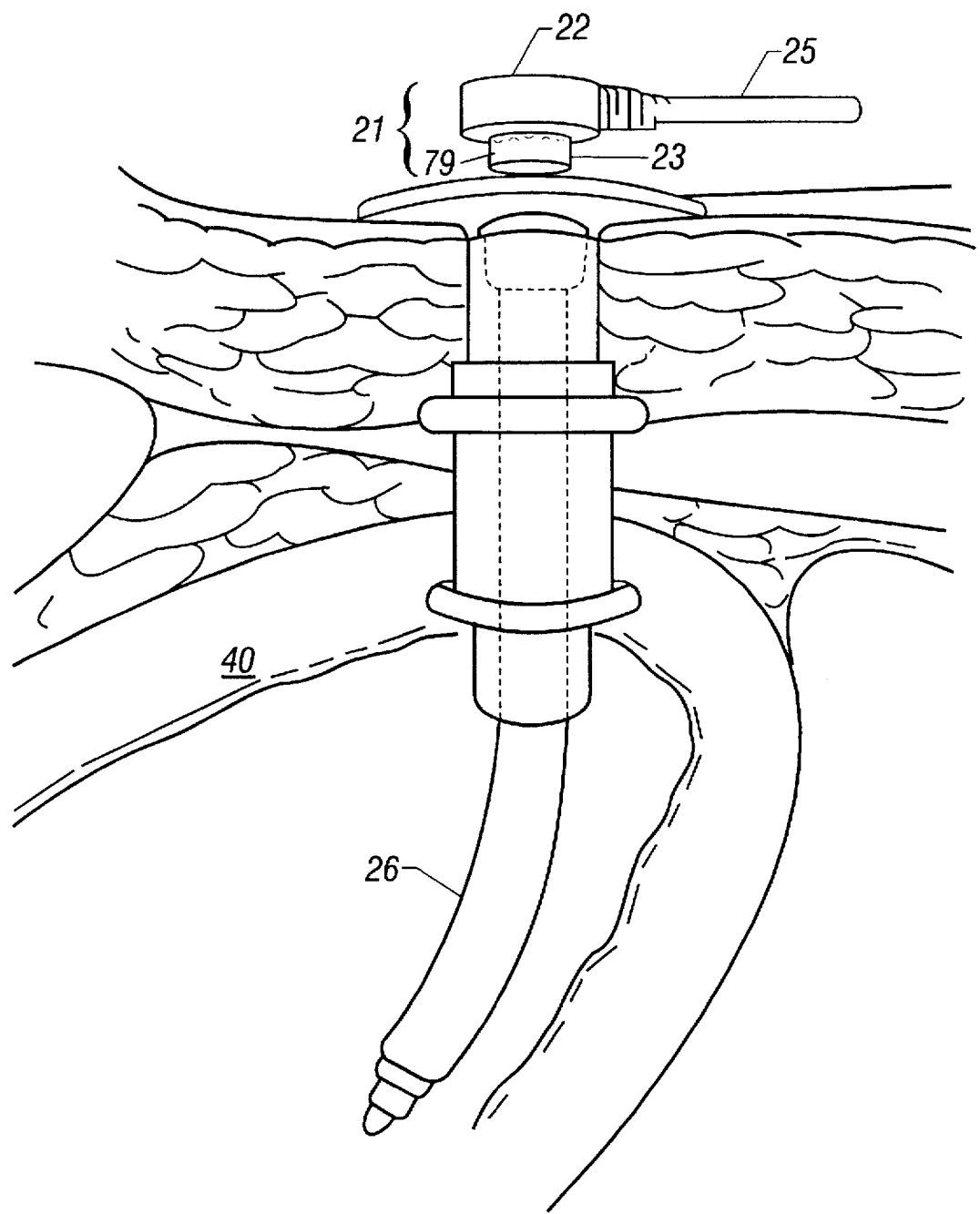
FIG. 6 is a side view of the deep implant cylinder, transcutaneous hollow cylinder, and cap and drainage tube assembly as installed at the end of the surgical implantation procedure.

A removable cap and drainage tube assembly 21 is insertable in the upper end of the transcutaneous hollow cylinder 20. As shown in FIG. 6, the removable cap and drainage tube assembly 21 comprises an antimicrobial filter 23 internally mounted in the cap 22 and an external drainage tube 25 attached to and extending outward from the cap 22. Cap and drainage tube assembly 21 can be fixed in the transcutaneous hollow cylinder 20 by a friction fit with retentive sutures or by other mechanical fixation mechanism.

In a preferred embodiment, the external drainage tube 25 is sufficiently long to extend into a leg bag attached to the patient's leg. The antimicrobial filter 23 serves as a bacterial filter 23 which prevents infected urine in the leg bag from reflexing back into the urinary bladder.

An internal drainage tube 26 extends downward from the inside of the cap 22. The internal drainage tube 26 is of sufficient length to extend into the patient's bladder when the cap is inserted into the transcutaneous hollow cylinder. A passageway extends through the removable cap 22 to permit fluid communication from the internal drainage tube 26 to the external drainage tube 25. In a preferred embodiment, the cap 22 is conically shaped, comprising a top surface and a bottom surface. The top surface of the cap 22 has a larger diameter than the bottom surface of the cap. The cap 22 is sized to fit snugly within the upper end of the transcutaneous hollow cylinder 20. The cap 22 may also be further secured to the transcutaneous hollow cylinder 20 by a mechanical mechanism or by the placement of a retentive suture below the flange around the transcutaneous hollow cylinder 20.

Figure 3B:
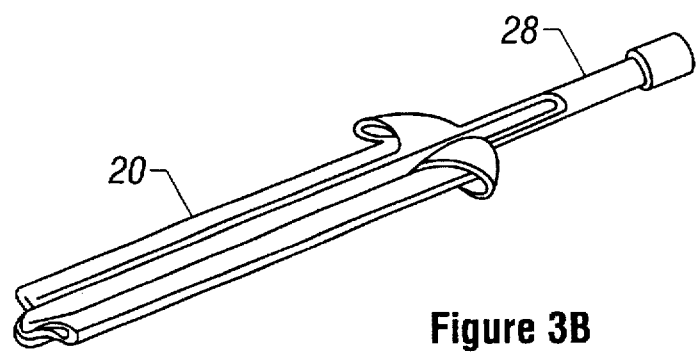
FIG. 3b is an isometric view of a transcutaneous hollow cylinder crimped onto a crimping tool.

Referring to FIG. 3a, the lower end 19b of transcutaneous hollow cylinder 20 is inserted into the deep implant cylinder 11. In a preferred method of assembling the present invention, a crimping tool 28 is used to insert transcutaneous hollow cylinder 20 into deep implant cylinder 11, and to ensure that there is a snug fit between transcutaneous hollow cylinder 20 and deep implant cylinder 11. As shown in FIG. 3b, the transcutaneous hollow cylinder 20 is crimped around the crimping tool 28 and then inserted into the deep implant cylinder. The crimping tool 28 is then removed from the transcutaneous hollow cylinder 20, thereby allowing the transcutaneous hollow cylinder to uncrimp and fit snugly within the deep implant, as shown in FIG. 4.

The internal drainage tube 26 is of sufficient diameter to house wires or electrodes, thereby providing for the use of the present invention with electrical, electronic, or electromagnetic, technology, including (1) iontophoresis, (2) process instrumentation, such as fluid level indicators, or (3) devices for generating electromagnetic fields in and around the bladder. The present invention may be used in conjunction with such electromagnetic field generators for the improved delivery and dispersion of drugs or medication to the bladder region.

As shown by the shaded area in FIG. 4, the lower portion of the deep implant cylinder 11b, stabilizing flange 15, and planar disc-like base 13 are coated on their exterior surface with a material suitable for bonding with biological tissue 30. In a preferred embodiment, the material suitable for bonding with biological tissue is a polytetrafluoroethylene polymer, such as that sold under the trademark Proplast®. Other suitable materials include porous biocompatible tissue bonding material such as porous polyurethane, Dacron® or other porous alloplastic material.

The present invention also relates to a surgical procedure for implanting the tissue bondable cystostomy tube. This procedure takes place in multiple phases which facilitate the bacterial resistant bonding of the tissue to the cystostomy tube. This tissue bonding entails biological bonding between the cystostomy tube and (1) the bladder detrusor muscle, and (2) the muscle and fascia of the abdominal wall. This tissue bonding resists urinary leakage and prevents skin bacteria from easily gaining access to the urinary bladder. As long as the abdominal stoma portion of the cystostomy tube remains capped, bacterial access to the bladder should not occur. Thus, the urinary infection problems associated with prior art cystostomy tubes are overcome by the present invention.

The first step in the method for implanting the tissue bondable cystostomy tube is to surgically implant the deep implant cylinder in the region of the bladder membrane 40, as shown in FIG. 1a. The uncoated silicone portion of the deep implant cylinder is placed in the subdermal area 42. During this implantation phase, a plug is inserted into the deep implant cylinder.

The skin is closed completely and aseptically in this initial surgical procedure thereby burying the device in the abdominal wall and bladder muscle, as shown in FIG. 1b. This burying minimizes risk of bacterial contamination while tissue ingrowth into the device occurs.

The deep implant cylinder is allowed to remain in the patient for a sufficient period of time for tissue bonding to occur. It is envisioned that several months will constitute a sufficient period of time for this tissue bonding to occur. During this time it is envisioned that a fibroblastic union will occur between the tissue and the polymer coated region of the deep implant cylinder and a fibrous non-bonded sheath will form around the uncoated nonporous portion of the deep implant cylinder.

After this tissue bonding has occurred, a circular portion of skin located above the deep implant cylinder is surgically excised. The plug or insert is then removed from the deep implant cylinder, as shown in FIG. 2.

In the second phase of the implantation procedure, the lower end of the transcutaneous hollow cylinder is slidably inserted into the deep implant cylinder until the lower end of the transcutaneous hollow cylinder is adjacent the bladder wall. In a preferred embodiment of the present invention, the transcutaneous hollow cylinder is crimped around a crimping tool and inserted into the deep implant while it is still crimped around the crimping tool. The crimping tool is then removed from the transcutaneous hollow cylinder, thereby allowing it to uncrimp and fit snugly within the deep implant cylinder, as shown in FIG. 4. The transcutaneous hollow cylinder is cut such that when its flanged end is flush with the patient's abdomen 44, its lower end extends the length of the deep implant cylinder without extending into the bladder.

This deep implant cylinder, transcutaneous hollow cylinder combination remains in the patient for several weeks to allow skin edges and subdermal tissue to heal and form a mature fibrous sheath around the transcutaneous tube.

Figure 7:
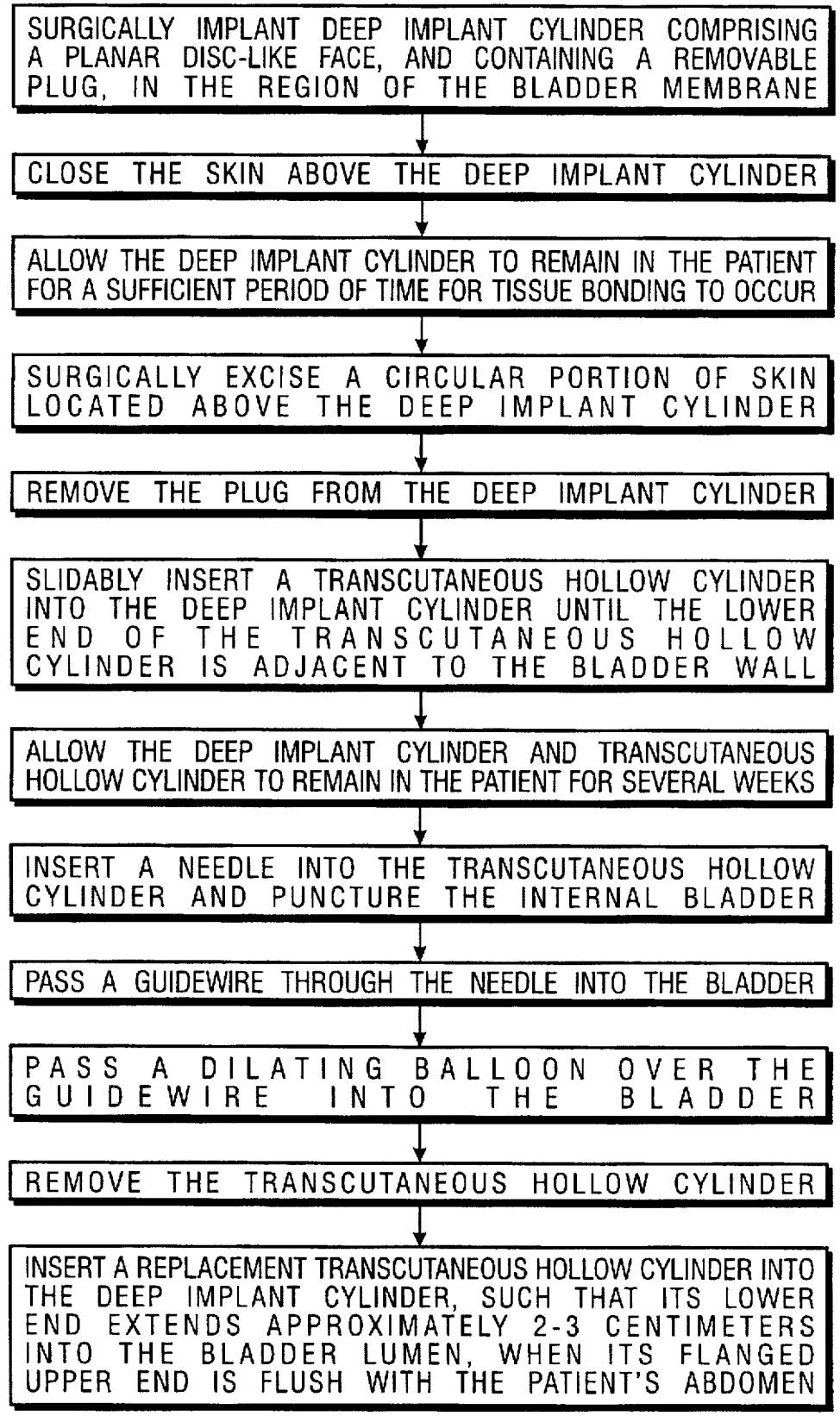
FIG. 7 is a block diagram of the surgical implantation procedure.

In the third phase of the implantation process, the bladder is filled with contrast media and monitored using conventional monitoring means such as fluoroscopy. A long thin piercing device, such as a needle is inserted into the transcutaneous hollow cylinder and passed through the bladder wall. A guidewire is passed through the needle into the bladder. A dilating balloon is passed over the guidewire into the bladder, as shown in FIG. 7. The existing transcutaneous hollow cylinder is removed and replaced by a longer transcutaneous hollow cylinder, having sufficient length such that when its flange is flush with the patient's abdomen, its lower end extends through the bladder wall approximately 2-3 centimeters into the bladder lumen, as shown in FIG. 6. An occlusive cap with internal and external drainage tubes is inserted into the upper end of the transcutaneous hollow cylinder. In a preferred embodiment, the cap is secured to the transcutaneous hollow cylinder by retentive sutures placed around the transcutaneous hollow cylinder below its flange or by mechanical fixation device such as male or female threads. In another preferred embodiment, the cap and drainage tube assembly is threadably affixed 79 to the upper end of the transcutaneous hollow cylinder as shown in FIG. 5.

Many modifications and variations may be made in the embodiments described herein and depicted in the accompanying drawings without departing from the concept of the present invention. Accordingly, it is clearly understood that the only and are not intended as a limitation upon the scope of the present invention.

What is claimed is:

1. A tissue bondable cystostomy tube comprising:

a. a deep implant cylinder comprising an upper portion and a lower portion terminating at a lower end point, the lower portion of said deep implant cylinder coated on its exterior surface with a porous biocompatible tissue bonding material;

b. a planar disc-like base coated on its exterior surface with a material suitable for bonding with biological tissue, said disc-like base extending radially outward from the lower end point of said deep implant cylinder and said base having a substantially constant radial dimension; and c. a transcutaneous hollow cylinder having an open lower end and a flanged upper end, the lower end of said transcutaneous hollow cylinder slidably received into the upper portion of said deep implant cylinder and extending to the lower end point of said deep implant cylinder.

2. The cystostomy tube of claim 1 further comprising a removable cap and drainage tube assembly affixed to the upper end of said transcutaneous hollow cylinder.

3. The cystostomy tube of claim 2 wherein the porous biocompatible tissue bonding material is polyurethane.

4. The cystostomy tube of claim 2 wherein the porous biocompatible tissue bonding material is Dacron®.

5. The cystostomy tube of claim 2 wherein the porous biocompatible tissue bonding material is a porous alloplastic material.

6. The cystostomy tube of claim 2 wherein the material suitable for bonding with biological tissue is a polytetrafluoroethylene polymer.

7. The cystostomy tube of claim 2 wherein said cap and drainage tube assembly comprises:

a. a conically-shaped cap having a top surface and a bottom surface, said top surface having a larger diameter than said bottom surface, and said cap is sized to fit snugly within the upper end of said transcutaneous hollow cylinder;

b. an external drainage tube attached to and extending outward from said cap; and c. an internal drainage tube extending downward from inside of said cap, said internal drainage tube being in fluid communication with said external drainage tube.

8. The cystostomy tube of claim 2 wherein said cap and drainage tube assembly is threadably affixed to the upper end of the transcutaneous hollow cylinder.

9. The cystostomy tube of claim 1 further comprising a stabilizing flange coated on its exterior surface with a material suitable for bonding with biological tissue and slidably mounted on the exterior surface of said deep implant cylinder.

10. The cystostomy tube of claim 1 wherein the transcutaneous hollow cylinder has an outer diameter sized to fit snugly within said deep implant cylinder.

11. The cystostomy tube of claim 1 wherein said planar disc-like base is integrally formed with said deep implant cylinder.

12. A tissue bonding cystostomy tube comprising:

a. a deep implant cylinder, having an upper portion and a lower portion terminating at a lower end point, said deep implant cylinder coated on the lower portion of its exterior surface suitable for bonding with biological tissue;

b. a planar disc-like base integrally formed with said deep implant cylinder and coated on its exterior surface with a material suitable for bonding with biological tissue, said disc-like base extending radially outward from the lower end point of said deep implant cylinder and said base having a substantially constant radial dimension;

c. a transcutaneous hollow cylinder having a lower end and a flanged upper end, the lower end of said transcutaneous hollow cylinder slidably received into the upper portion of said deep implant cylinder and extending to the lower end point of said deep implant cylinder;

d. a stabilizing flange coated on its exterior surface with a material suitable for bonding with biological tissue and slidably mounted on the exterior surface of said deep implant cylinder; and e. a removable cap and drainage tube assembly slidably insertable within the upper end of said transcutaneous hollow cylinder.

13. The cystostomy tube of claim 12 wherein said flanged upper end comprises a V-shaped notch.

* * * * *